(12) United States Patent
Eaton et al.

(10) Patent No.: US 8,484,393 B2
(45) Date of Patent: Jul. 9, 2013

(54) SYSTEMS AND METHODS FOR SELECTING PARAMETERS USED IN A PORTABLE PATIENT MONITOR

(75) Inventors: Scott Eaton, Criarcliff Manor, NY (US); Jack Balji, Mahaw, NJ (US); James Fidacaro, Mountain Lakes, NJ (US); Frank Menzel, Oakland, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 0 days.

(21) Appl. No.: 13/588,915

(22) Filed: Aug. 17, 2012

(65) Prior Publication Data
US 2012/0317327 A1    Dec. 13, 2012

Related U.S. Application Data

(63) Continuation of application No. 12/545,393, filed on Aug. 21, 2009, now Pat. No. 8,266,349.

(51) Int. Cl.
*G06F 3/00* (2006.01)
*G06F 13/12* (2006.01)
*G06F 13/00* (2006.01)
*H04L 12/28* (2006.01)
*A61B 5/00* (2006.01)

(52) U.S. Cl.
USPC ............... 710/62; 710/8; 710/14; 710/303; 710/304; 370/254; 600/300; 600/301

(58) Field of Classification Search
USPC ... 710/8, 14, 62, 303–305; 370/254; 713/173; 455/404.2; 600/300–301, 484
See application file for complete search history.

(56) References Cited

U.S. PATENT DOCUMENTS

| 5,375,604 | A | 12/1994 | Kelly et al. |
| 5,463,742 | A | 10/1995 | Kobayashi |
| 5,640,953 | A | 6/1997 | Bishop et al. |
| 5,936,539 | A | 8/1999 | Fuchs |
| 8,266,349 | B2 * | 9/2012 | Eaton et al. ............. 710/62 |
| 8,405,608 | B2 * | 3/2013 | Al-Ali et al. ............ 345/158 |
| 2003/0078811 | A1 * | 4/2003 | Cole et al. ............... 705/3 |
| 2003/0200371 | A1 | 10/2003 | Abujbara |
| 2004/0147818 | A1 * | 7/2004 | Levy et al. ............. 600/300 |
| 2005/0033124 | A1 | 2/2005 | Kelly et al. |

(Continued)

FOREIGN PATENT DOCUMENTS
WO    2005001739 A2    1/2005

OTHER PUBLICATIONS

"Seamless Patient Transport," Innovations-report Nov. 20, 2008, pp. 1-2, Online, http://www.innovationsreport.com/html/reports/medical_technology/seamless_patient_transport_122752.html; Jun. 24, 2009.

(Continued)

*Primary Examiner* — Idriss N Alrobaye
*Assistant Examiner* — Henry Yu
(74) *Attorney, Agent, or Firm* — Kory D. Christensen; Stoel Rives LLP

(57) ABSTRACT

A patient monitoring system includes a patient monitor and a plurality of docking stations. Each docking station is associated with a set of patient monitor configurations. Interfacing the patient monitor with a particular docking station allows a user to select one or more of the set of patient monitor configurations associated with the particular docking station for use in the patient monitor.

17 Claims, 6 Drawing Sheets

U.S. PATENT DOCUMENTS

| | | |
|---|---|---|
| 2006/0094936 A1* | 5/2006 | Russ .................. 600/300 |
| 2007/0271115 A1 | 11/2007 | Baldus et al. |
| 2007/0281661 A1 | 12/2007 | Del Signore |
| 2008/0046735 A1 | 2/2008 | Nedeltchev et al. |
| 2008/0183910 A1 | 7/2008 | Natoli et al. |
| 2009/0213756 A1 | 8/2009 | Reddy et al. |
| 2011/0047298 A1 | 2/2011 | Eaton et al. |

OTHER PUBLICATIONS

"Transient." Definition and More from the Free Merriam-Webster Disctionary. (2011). Accessed Nov. 10, 2011 from http://www.merriam-webster.com/dictionary/transient?show=1&t=2.

Office Action mailed Jun. 7, 2011 as received in U.S. Appl. No. 12/545,393.

Office Action mailed Nov. 16, 2011 as received in U.S. Appl. No. 12/545,393.

Office Action mailed Feb. 16, 2012 as received in U.S. Appl. No. 12/545,393.

Notice of Allowance mailed Jul. 31, 2012 as received in U.S. Appl. No. 12/545,393.

* cited by examiner

FIG. 4
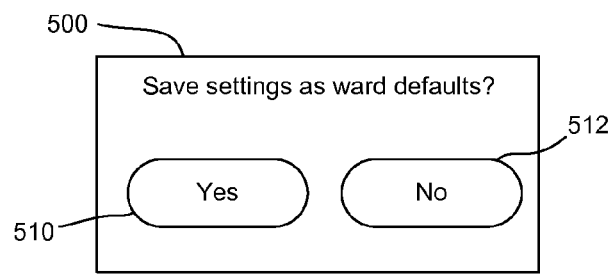
FIG. 5
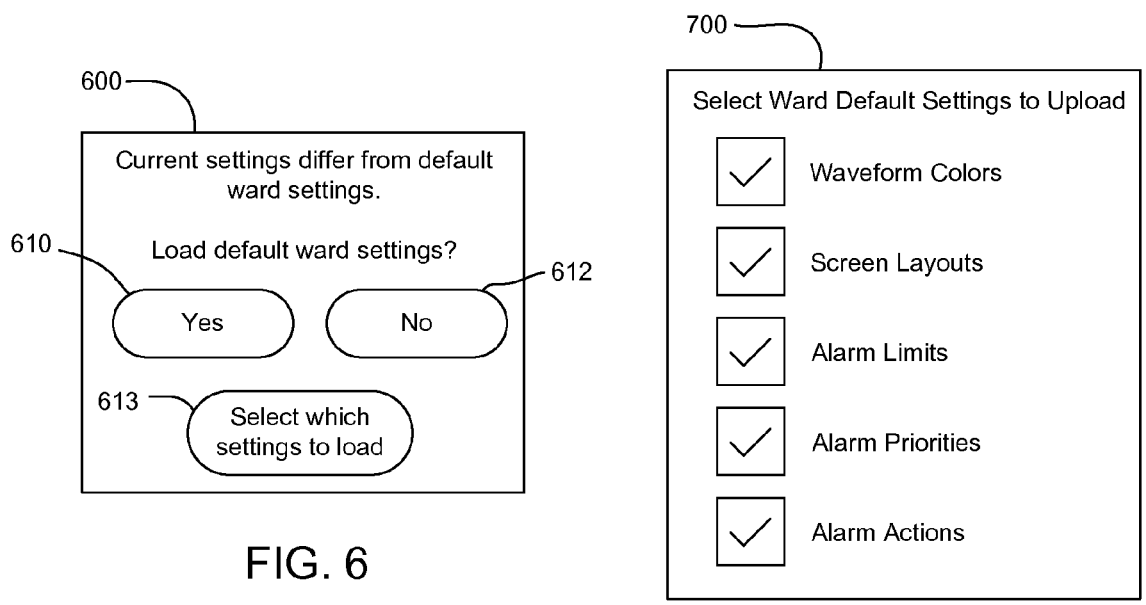
FIG. 6
FIG. 7

SYSTEMS AND METHODS FOR SELECTING PARAMETERS USED IN A PORTABLE PATIENT MONITOR

CROSS-REFERENCE TO RELATED APPLICATIONS

This application is a continuation of U.S. patent application Ser. No. 12/545,393, filed Aug. 21, 2009, for "Systems and Methods for Selecting Parameters used in a Portable Patient Monitor", the entirety of which is incorporated by reference herein.

TECHNICAL FIELD

The present disclosure relates to patient monitor systems.

SUMMARY

A system according to one embodiment includes a patient monitor and a plurality of docking stations. Each docking station is associated with a set of patient monitor configurations. Interfacing the patient monitor with a particular docking station allows a user to select one or more of the set of patient monitor configurations associated with the particular docking station for use in the patient monitor.

Additional aspects and advantages will be apparent from the following detailed description of preferred embodiments, which proceeds with reference to the accompanying drawings.

BRIEF DESCRIPTION OF THE DRAWINGS

FIG. 4 graphically represents a button for storing a current set of configuration settings to a docking station according to one embodiment.

FIG. 5 graphically illustrates a graphical user interface for saving a current set of configuration settings as a default for a current patient monitoring location according to one embodiment.

FIG. 6 graphically illustrates a graphical user interface for prompting a user to load default configuration settings according to one embodiment.

FIG. 7 graphically illustrates a graphical user interface for allowing a user to select among a plurality of default settings to load into a patient monitor according to one embodiment.

DETAILED DESCRIPTION

Figure 1:
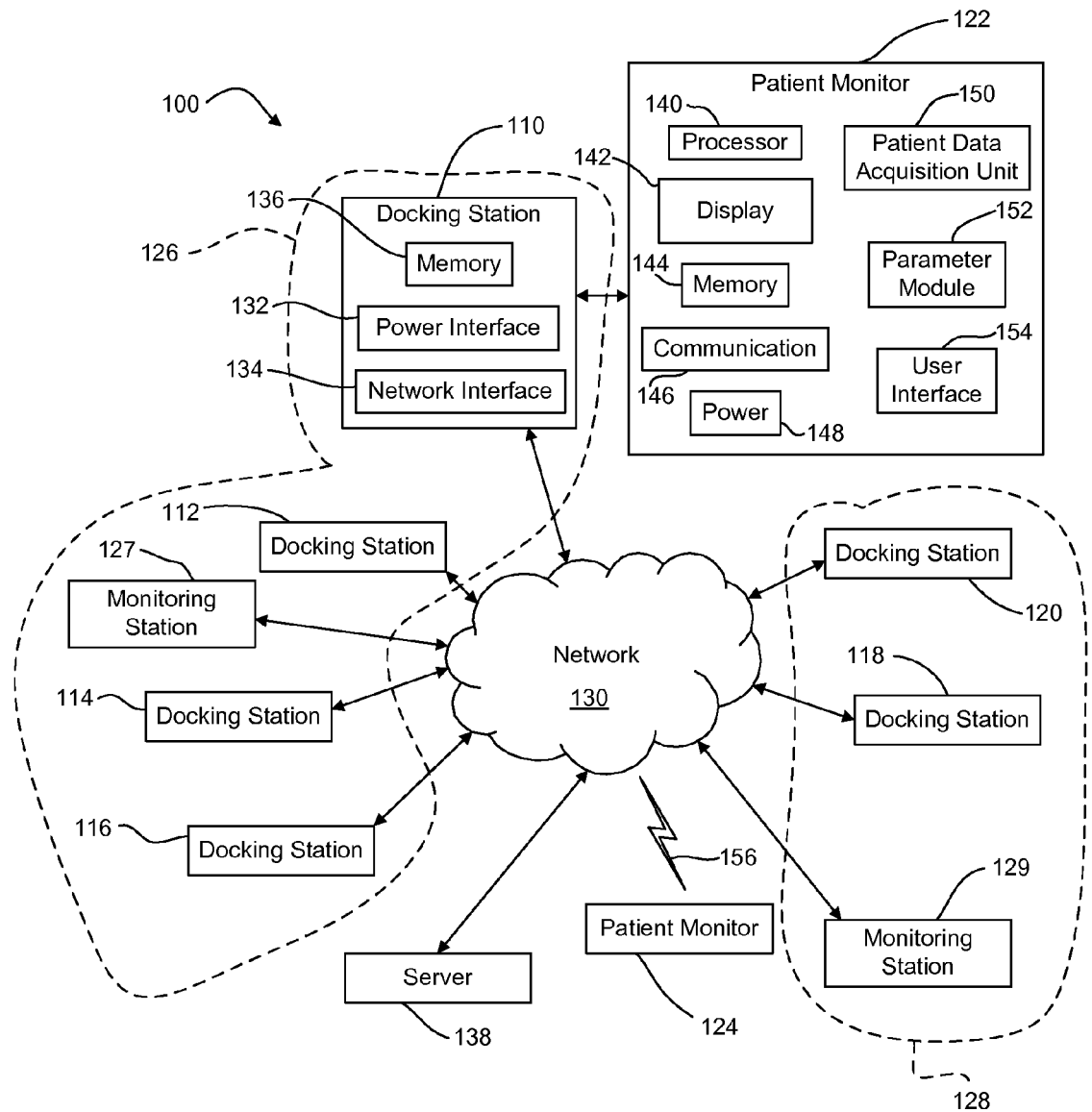
FIG. 1 is a block diagram of a patient monitoring system according to one embodiment.

Patient monitors are used to acquire, analyze, and display data from sensors attached to a patient. The data may include, for example, pulse, temperature, respiration, blood pressure, blood oxygen, electrocardiogram, and other patient parameters. It is often desirable to continuously monitor patient parameters when transporting patients, including while transporting patients between hospital wards. Transporting patients between hospital wards, however, may require nurses or other hospital staff to spend time and effort reattaching the patient from a portable monitoring system to a fixed monitoring system and/or reconfiguring a patient monitor with configuration settings used by the different wards. The patient monitor configuration settings may be defined by administrators of each ward and may be based on hospital-specific practices and/or general (e.g., statewide or nationwide) standard practices. For example, an emergency room may be required to monitor a different set of patient parameters or use different display settings (e.g., brightness or colors) than that of a catheterization lab or an intensive care unit.

Thus, when a portable patient monitor is introduced into a patient ward, the patient monitor generally needs to be configured for that particular ward's custom settings. This may be accomplished, for example, by accessing the patient monitor's menu system and configuring the patient monitor. Alternatively, the patient monitor may be configured by downloading a configuration from an external storage device or from a network. The configuration process can be time consuming. If it is required to manually load the configuration data from a storage device or a network, the user may forget to load the configuration data and the patient monitor will not be set to the ward's custom configuration. If the user is required to enter the configuration data manually into the patient monitor, the configuration process may also be error prone.

Thus, in one embodiment, a ward's custom configuration is associated with a docking station. For example, in one embodiment, the ward's custom configuration settings may be stored in a memory device in the docking station. Upon connection to the docking station, the patient monitor may load some or all of the ward's custom configuration settings from the memory device. In another embodiment, the docking station may be associated with a unique identifier. Upon connection to the docking station, the monitor may establish a connection with a network and download some or all of the ward's custom configuration settings from a server based on the unique identifier.

Because a user (e.g., a nurse) may spend a substantial amount of time configuring a patient monitor with custom settings for a particular patient, it may be undesirable for some or all of the settings to be automatically updated to the default configuration settings of a new ward. For example, when a patient is transported from an operating recovery room to an intensive care unit, the user may want to keep at least some of the settings configured in the operating recovery room based on the particular patient's condition. Thus, whenever a user connects a patient monitor to a docking station in a new ward according to certain embodiments, the patient monitor prompts the user to change the monitor's settings to the new ward's default settings. If the user indicates that an update to the new ward's default settings is desired, the monitor automatically loads the new ward's default settings (e.g., from either the docking station or a network server) and configures itself according to the loaded settings. In certain such embodiments, the user may select only a portion of the new ward's default settings, while maintaining other current settings. Because the update to the new ward's default settings is not automatic, a user may selectively maintain all or part of a custom configuration previously established for a particular patient.

In addition, or in other embodiments, certain docking stations are associated with transient locations, such as a radiology department, where a patient may be expected to remain for a relatively short period of time before returning to his or her room or before being transported to another area of the hospital. In such embodiments, the patient monitor is configured to determine whether or not a currently connected docking station is a transient docking station. If the patient monitor determines that the currently connected docking station is a non-transient docking station associated with default configuration settings, then the patient monitor prompts the user to update the monitor's settings with the default settings associated with the ward of the currently connected docking station. If, however, the patient monitor determines that the currently connected docking station is a transient docking station, the monitor does not prompt the user to update the patient monitor's settings with those associated with the currently connected docking station, if any. In some embodiments, transient docking stations are not associated with a set of default monitor settings.

The patient monitor configuration settings may include, for example, selection of displayed waveforms, waveform display priority, display layout including definitions of hot keys or user configuration buttons, waveform colors, speaker volume, brightness, alarm priorities, alarm limits, and/or alarm responses. The alarm responses may include, for example, defining which alarms require paging a doctor, which alarms require event logging, and/or which alarms require information to be printed or transmitted to a remote monitoring station.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or detailed description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform the processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/computer-readable medium suitable for storing electronic instructions.

FIG. 1 is a block diagram of a patient monitoring system 100 according to one embodiment. The patient monitoring system 100 includes a plurality of docking stations 110, 112, 114, 116, 118, 120, and one or more patient monitors 122, 124. In the example embodiment shown in FIG. 1, the docking stations 110, 112, 114 are associated with a first patient monitoring location 126, and the docking stations 118, 120 are associated with a second patient monitoring location 128.

The first and second patient monitoring locations 126, 128 may be different hospital wards. For example, the first or second patient monitoring locations 126, 128 may correspond to surgery, day surgery, urology, respiratory, transplant, dialysis, renal, oncology, radiology, catheterization, or any other ward, unit, or department of the hospital. A first monitoring station 127 may be used to remotely monitor patients in the first patient monitoring location 126 and a second monitoring station 129 may be used to remotely monitor patients in the second patient monitoring location 128. The first patient monitoring location 126 is associated with a first set of default configuration settings and the second patient monitoring location 128 is associated with a second set of default configuration settings. In this example embodiment, the first set of default configuration settings is different than the second set of default configuration settings.

The patient monitors 122, 124 are mobile to allow patients to be continuously monitored during transportation between the first and second patient monitoring locations 126, 128 without being disconnected from the respective patient monitor 122, 124. Accordingly, the patient monitors 122, 124 are each configured to be selectively coupled with and selectively decoupled from any of the respective docking stations 110, 112, 114, 116, 118, 120.

For illustrative purposes, the patient monitor 122 is shown as being coupled to the docking station 110. In certain embodiments, the docking stations 110, 112, 114, 116, 118, 120 provide the respective patient monitors 122, 124 with power and/or a connection to a network 130, such a hospital's local area network (LAN) and/or the Internet. Accordingly, the docking station 110 is illustrated as including a power interface 132 and a network interface 134. The power interface 132 may be configured to convert an alternating current (AC) power signal to a direct current (DC) power signal and/or provide power signal conditioning for the coupled patient monitor 122. The network interface 134 may include, for example, an Ethernet communication controller to allow the coupled patient monitor 122 to communicate through the network 130 through the docking station 110. The network interface 134 maybe associated with a media access control (MAC) address.

In certain embodiments, the docking station 110 may also include a memory device 136. The memory device 136 may include non-volatile random access memory (RAM) that provides addressable storage and may be used in certain embodiments to store the default configuration settings associated with the first patient monitor location 126. In addition, or in other embodiments, the memory device 136 stores a unique identifier associated with the first patient monitoring location 126. The patient monitor 122 reads the unique identifier from the memory device 136. In one embodiment, the patient monitor 122 includes a radio frequency identification (RFID) (not shown) for reading the unique identifier from the docking station 110. In other embodiments, the patient monitor 122 directly accesses an addressable memory location in the memory device 136 of the docking station 110 to access the unique identifier. The patient monitor 122 then transmits the unique identifier to a server 138 through the network interface 134. In response, the server 138 transmits the default configuration settings corresponding to the first patient monitoring location 126 to the patient monitor 122 through the network interface 134. In certain such embodiments, the server also stores the default configuration settings in the memory device 136 as a backup in case communication through the network is lost or is temporarily unavailable. Although the memory device 136 is illustrated in FIG. 1 as a separate unit, an artisan will recognize from the disclosure herein that the network interface may include memory for storing a unique identifier such as a MAC address.

The patient monitor 122, according to the example embodiment illustrated in FIG. 1, includes a processor 140, a display device 142, a memory device 144, a communication device 146, a power module 148, a patient data acquisition unit 150, a parameter module 152, and a user interface 154. The processor 140 is configured to process patient data signals received through the patient data acquisition unit 150 and to display the patient data signals (e.g., as waveforms and/or numerical readouts) on the display device 142. Although not shown, the patient data acquisition unit 150 receives the patient data signals from one or more sensors attached to a patient. The patient data acquisition unit 150 may be configured to process the acquired patient data signals in cooperation with the processor 140.

The patient monitor 122 may store the patient data signals in the memory device 144 along with other data. For example, the patient monitor 122 may store a current set of configuration settings in the memory device 144. In one embodiment, the patient monitor 122 replaces the current set of configuration settings in the memory device 142 with the default configuration settings corresponding to the first patient monitoring location 126 received from the memory device 136 of the docking station 110 or from the server 138. In another embodiment, the patient monitor 122 maintains the current set of configuration settings as it stores the default configuration settings for the first patient monitoring location 126 in a different memory location in the memory device 144. Thus, the user can select which set of stored configuration settings to use. In one embodiment, the set of configuration settings maintained in the memory device 144 includes default settings used by the patient monitor 122.

The communication device 146 is configured to communicate with the network 130 through the network interface 134 of the docking station 110. In certain embodiments, the communication device 146 is also configured to wirelessly communicate with the network 130 when the patient monitor 122 is not coupled to any of the docking stations 110, 112, 114, 116, 118, 120. For example, as illustrated in the example embodiment of FIG. 1, the patient monitor 124 automatically establishes a communication link 156 with the network 130 as a user transports the patient monitor 124 from the first patient monitoring location 126 to the second patient monitoring location 128.

The power module 148 receives a power signal from the power interface 132 of the docking station 110. The power module 148 provides any necessary power conversions and distributes power throughout the patient monitor 122. The power module 148 may include a battery that is charged through the power interface 132 while the patient monitor 122 is coupled to the docking station 110.

The parameter module 152 cooperates with the processor 140 to detect a coupling of the patient monitor 122 to the docking station 110. In response to a predetermined condition, the parameter module 152 prompts the user (e.g., through the user interface 154) to select one or more of the default configuration settings associated with the first patient monitoring location 126. In response to user selections through the user interface 154, the parameter module 152 loads the selected default configuration settings into the memory device 144 and configures the patient monitor 122 accordingly.

The predetermined condition may include a determination by the parameter module 152 and/or processor 140 that the first patient monitor location 126 is a non-transient hospital ward. For example, the first patient monitor location 126 may be an intensive care unit where the patient is expected to remain for a period of hours or days. The parameter module 152 and/or processor 140 may be further configured to detect that the patient monitor 122 has been coupled to the transient docking station 116. In response to the determination of the transient location, the parameter module 152 and/or processor 140 may maintain a current set of configuration settings in disregard to one or more default settings, if any, associated with the transient patient monitor location. When the patient monitor 122 is coupled to the transient docking station, the user is not prompted to change the patient monitor's current set of configuration settings. Thus, the user (e.g., a nurse) in a particular ward does not need to worry about the settings being changed when, for example, the patient is sent for chest x-rays.

In addition, or in other embodiments, the predetermined condition may include a determination by the parameter module 152 and/or processor 140 that a current set of configuration settings is different than the default configuration settings associated with the first patient monitor location 126. Thus, the user is not prompted to change settings when the patient monitor changes docking stations within the same patient monitoring location (e.g., the patient is assigned a different bed within the same ward), or when the patient monitor is transported between patient monitoring locations that have the same default configuration settings.

The predetermined condition may also include a determination by the parameter module 152 and/or processor 140 that one or more of the default configuration settings associated with the first patient monitoring location 126 are optional settings. Thus, the user is not prompted and the default configuration settings are automatically loaded when all of the default configurations settings are required (e.g., by an administrator over the first patient monitoring location 126).

Further, the predetermined condition may include a determination by the parameter module 152 and/or processor 140 that the current settings include an unprotected setting that conflicts with one or more default configuration settings. For example, a current set of configuration settings may be protected such that a sufficient authorization level is required (e.g., by an administrator or supervisor) to change or ignore the protected settings. If a current setting is protected, then the user is not prompted to change the setting.

An artisan will recognize from the disclosure herein that the parameter module 152 and/or the patient data acquisition unit 150 may be combined with the processor 140 into a single unit. Further, the processor 140, parameter module 152, and/or patient data acquisition unit 150, either combined or separately, may include a special purpose processor configured to perform the processes described herein. In another embodiment, the processor 140, parameter module 152, and/or patient data acquisition unit 150, either combined or separately, may include a general purpose processor configured to execute computer executable instructions (e.g., stored in a computer-readable medium (such as the memory device 144) to perform the processes described herein.

Figure 2:
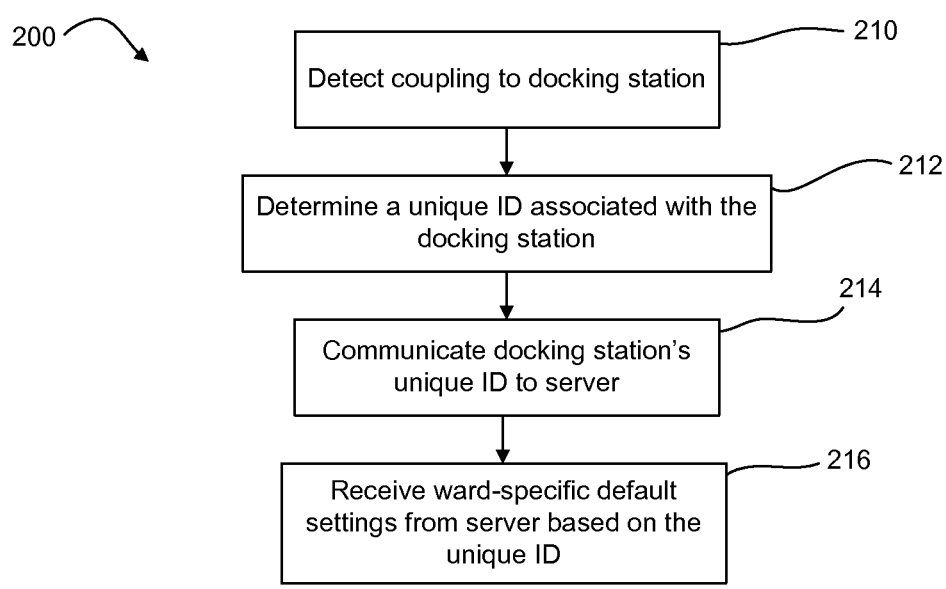
FIG. 2 is a flowchart of a process for updating the configuration settings of a patient monitor from a network server according to one embodiment.

FIG. 2 is a flowchart of a process 200 for updating the configuration settings of a patient monitor from a network server according to one embodiment. The process 200 includes detecting 210 a coupling of the patient monitor to a docking station and determining 212 a unique identifier (ID) associated with the docking station. As discussed above, the unique ID may be stored in the docking station's memory and/or may be a MAC address. The process 200 further includes communicating 214 the docking station's unique ID to the network server and receiving 216 ward-specific default settings from the server based on the unique ID.

As discussed below with respect to FIGS. 3A and 3B, certain embodiments of the process 200 shown in FIG. 2 also include determining whether the settings of a particular docking station should be updated and/or querying the user to determine which if any of the ward-specific default settings to load.

In other embodiments, ward-specific default settings may be loaded directly from a server without first determining a unique ID associated with a particular docking station. In certain such embodiments, a user may be able to store settings in, and retrieve settings from, a server regardless of whether or not the patient monitor is even connected to a docking station. For example, a user may choose from a menu of available configurations to load from the server. In addition, after configuring a patient monitor, the user may have the ability to save the configuration directly to the server without a docking station or without associating the configuration with any particular docking station. For example, the user (e.g., a doctor or nurse) may have a preferred configuration that the user does not want to manually create and store on every monitor that the user uses. Instead, the user may save the desired configuration to the server and load it (from the server) onto whichever patient monitor that the user is currently using. This may also be used for setting up the system wherein a user sets up a patient monitor, loads the configuration to the server, goes to the next monitor and downloads the configuration from the server, saves the configuration to the current monitor or docking station, and continues on to the next monitor.

Figure 3A:
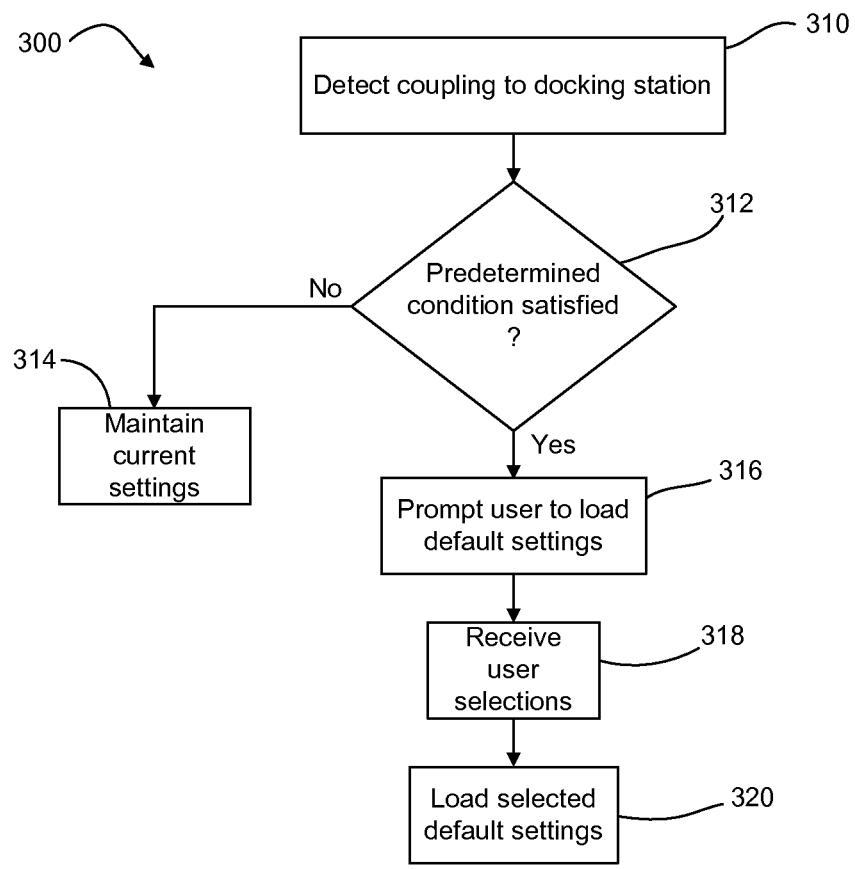
FIG. 3A is a flowchart of a method for use in a portable patient monitoring system according to one embodiment.

FIG. 3A is a flowchart of a method 300 for use in a portable patient monitoring system according to one embodiment. The method 300 includes detecting 310 a coupling of a portable patient monitor to a docking station and querying 312 whether a predetermined condition has been satisfied. If the predetermined condition has not been satisfied, the method 300 includes maintaining 314 the current settings of the patient monitor. If, however, the predetermined conditions have been satisfied, the method 300 includes prompting 316 a user to load default settings associated with a patient monitoring location of the docking station. The method 300 further includes receiving 318 user selections indicating which, if any, of the default settings to use, and loading 320 the selected default settings into the patient monitor.

Figure 3B:
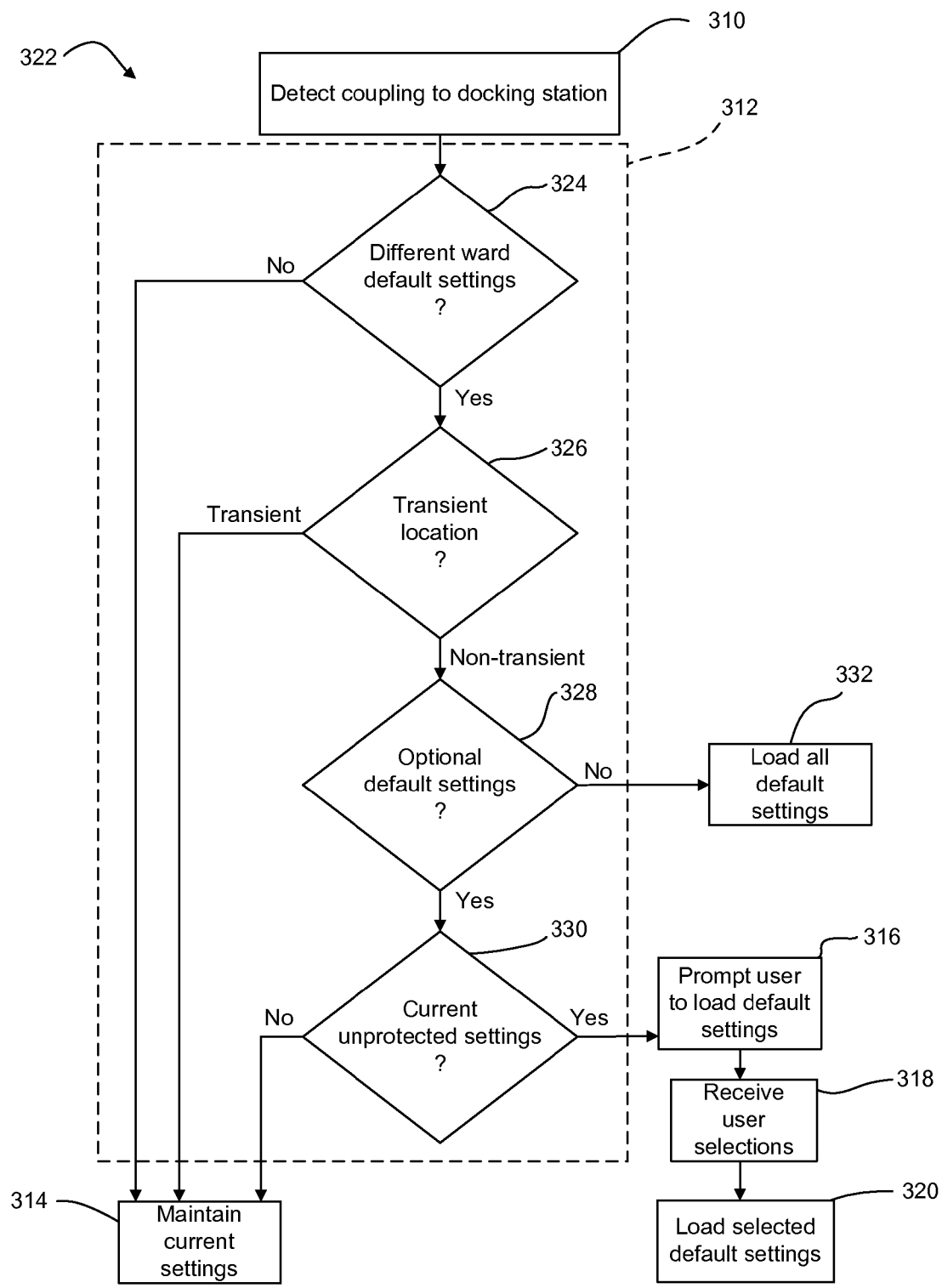
FIG. 3B is a flowchart of a method for use in a portable patient monitoring system according to other embodiments.

FIG. 3B is a flowchart of a method 322 for use in a portable patient monitoring system according to other embodiments. As discussed above with respect to the method 300 of FIG. 3A, the method 322 shown in FIG. 3B includes detecting 310 a coupling of a portable patient monitor to a docking station. In the method 322 shown in FIG. 3B, however, illustrates various options for querying 312 whether a predetermined condition has been satisfied. One or more of the different illustrated options 324, 326, 328, 330 may be used in any combination. For example, the method 322 may include querying 324 whether different ward default settings are required as compared to a current set of default settings in the patient monitor. If the ward default settings are not different than the current set of settings in the patient monitor, then the method 322 includes maintaining 314 the current settings of the patient monitor.

The method may also include querying 326 whether the coupled docking station corresponds to a transient location. If the coupled docking station is a transient location, the method 322 includes maintaining 314 the current settings of the patient monitoring system. If the coupled docking station is a non-transient location, the method 322 proceeds toward prompting 316 the user to load the default settings. The method 322 may also include querying 328 whether there are any optional default settings corresponding to the patient monitoring location. If none of the default settings for the patient monitoring location is optional, the method 322 includes loading 332 all of the default settings without prompting the user. The method 322 may also include querying 330 whether any of the current settings are unprotected. If all of the current settings are protected, then the method 322 includes maintaining 314 the current settings of the patient monitoring system. If, on the other hand, one or more of the current settings are unprotected, then the method 322 includes prompting 316 the user to load the default settings. The method 322 further includes receiving 318 user selections indicating which, if any, of the default settings to use, and loading 320 the selected default settings into the patient monitor.

In one embodiment, a user may store a current set of configuration settings to a connected docking station or to a network server by pressing a button on the patient monitor. For example, FIG. 4 graphically represents a button 400 for storing a current set of configuration settings to a docking station according to one embodiment. An artisan will recognize from the disclosure herein that the configuration settings may be stored to other locations or devices other than (or in addition to) the docking station. For example, the configuration settings may be stored in, and retrieved from, a USB flash, a hard drive, or any other type of memory device.

As another example, FIG. 5 graphically illustrates a graphical user interface 500 for saving a current set of configuration settings as a default for a current patient monitoring location according to one embodiment. The graphical user interface allows a user to select a "yes" control 510 to save the settings as ward defaults or a "no" control 512 to ignore the prompt. As discussed above, selecting the "yes" control 510 in the user interface 500 may save the current settings to a memory device in the connected docking station, to a network server, or both.

FIG. 6 graphically illustrates a graphical user interface 600 for prompting a user to load default configuration settings according to one embodiment. The graphical user interface 600 includes a "yes" control 610 that the user may select to load all of the default configuration settings and a "no" control 612 that the user may select to load none of the default configuration settings. The graphical user interface 600 also includes another control 613 that a user may select to selectively load a subset of the default configuration settings corresponding to the patient monitoring location. For example, if the user selects this control 613, the patient monitor may present the user with the user interface 700 shown in FIG. 7, which allows the user to select (e.g., illustrated with check marks) which settings to load, including waveform colors, screen layouts, alarm limits, alarm priorities, and alarm actions. Artisans will recognize from the disclosure herein that many other default configuration settings may also be selected.

Figure 8:
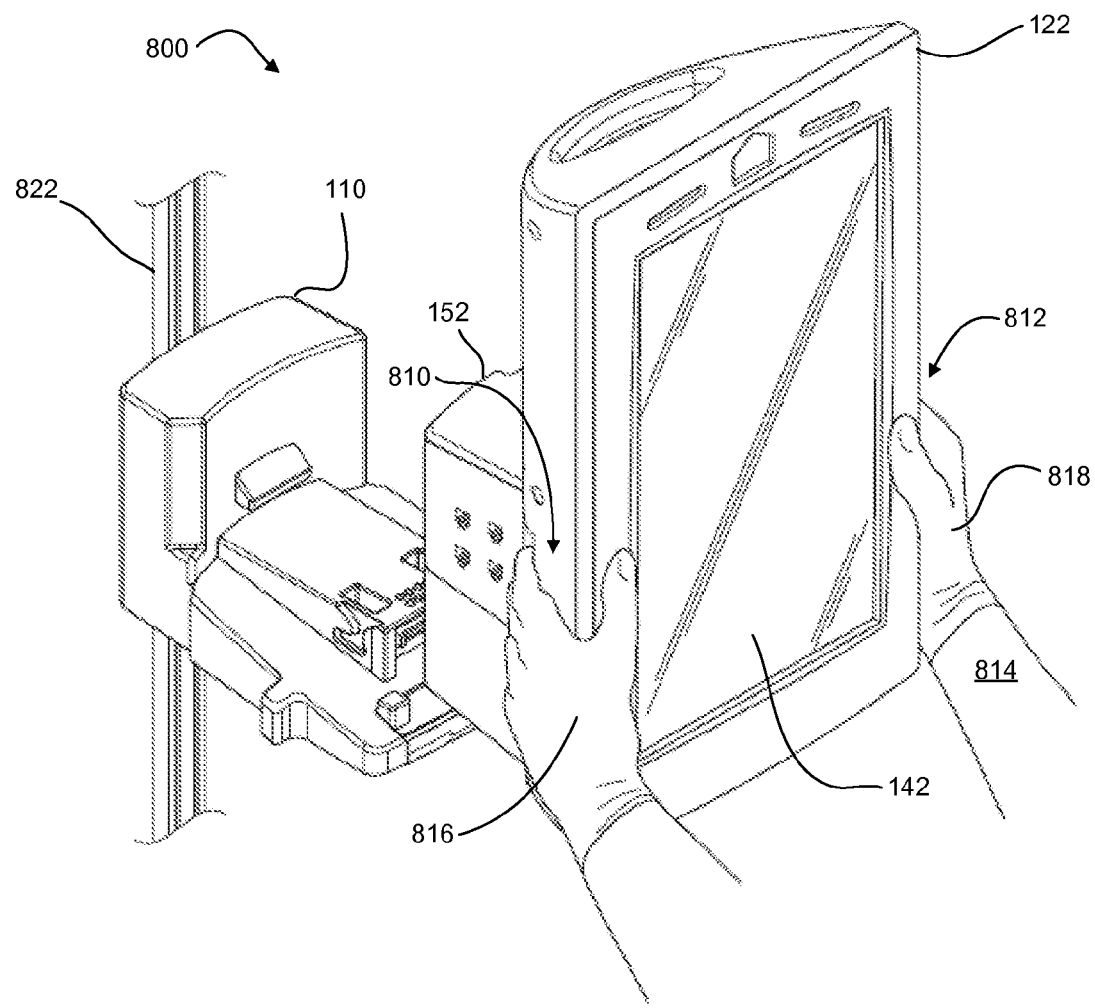
FIG. 8 is a perspective view of a patient monitor system according to one embodiment.

FIG. 8 is a perspective view of a patient monitor system 800 according to one embodiment. The embodiment shown in FIG. 8 is provided by way of example and an artisan will understand from the disclosure herein that any portable patient monitoring system may be used with the embodiments disclosed herein. The system 800 includes a patient monitor 122, a patient parameter module 152, and a docking station 110. The patient monitor 122 can be configured to selectively couple with and decouple from the docking station 110, and the patient parameter module 152 can be configured to selectively couple with and decouple from the patient monitor 122. The coupling between the patient monitor 122 and the docking station 110, or between the patient parameter module 152 and the patient monitor 122, can be mechanical, electrical, optical, and/or any other suitable variety. For example, the coupling can be for physical union, power transfer, and/or communication.

The patient monitor 122 may include one or more gripping regions 810, 812 that are configured to aid in coupling and decoupling the patient monitor 122 from the docking station 110. For example, a medical practitioner 814 can firmly grasp with his or her hands 816, 818 the gripping regions 810, 812 during removal of the patient monitor 122 from the docking station 110. When the patient monitor 122 is separated from the docking station 110, the full weight of the patient monitor 122 can be supported by a grip of the medical practitioner 814 on the gripping regions 810, 812. In some embodiments, the medical practitioner 814 can bear the full weight of the patient monitor 122 by holding only one of the gripping regions 810, 812.

The patient monitoring system 800 may include one or more actuators (not shown) which, when actuated, permit release of the patient monitor 122 from the docking station 110. The actuators can be integrated into the gripping regions 810, 812 or other portions of the patient monitor 122 so as to permit for convenient and continuous-movement dismounting of the patient monitor 122. For example, in some embodiments, a practitioner 814 can actuate an actuator using a hand 816, 818 while that hand 816, 818 is simultaneously holding a respective gripping region 810, 812.

In FIG. 8, the patient monitor 122 is illustrated as having been removed from the docking station 110. A front surface of the patient monitor 122 can include a display 142 that is configured to display information in a visually perceivable format. The screen 142 may be of any suitable variety, including those presently known and those yet to be devised. For example, the screen 142 may include a liquid crystal display (LCD) panel. In some embodiments, the screen 142 may be configured to receive information or otherwise interact with a medical practitioner. For example, the screen 142 may include a touch screen.

In some embodiments, the screen 142 is configured to display information in a predetermined orientation that correlates with a docking orientation of the patient monitor 122. Information can be displayed on the screen 142 in an upright orientation when the patient monitor 122 is coupled with the docking station 110. For example, in the configuration depicted in FIG. 8, text, graphs, or other information can be displayed via the screen 142 in an orientation that is natural for reading.

The patient monitor 122 may include one or more ports for receiving or delivering information, which can include one or more serial ports, USB ports, Ethernet ports, DVI ports, or any other suitable variety of ports, interfaces, or connectors. In some embodiments, information received via one or more of the ports can be displayed on the screen 142.

At least a portion of the information displayed by the patient monitor 122 may represent information received from a patient or that otherwise relates to the patient. For example, in some embodiments, one or more sensors (not shown) are connected to the patient to sense a particular parameter, and information obtained via the one or more sensors is delivered to the patient parameter module 152. The sensors may deliver information to the patient parameter module 152 via one or more cables (not shown) connected to one or more ports.

The patient parameter module 152 may be configured to process the information it receives from a sensor and deliver it to the patient monitor 122, which can display the processed information. In some embodiments, the patient monitor 122 may further process the information prior to displaying it. The patient monitor 122 may also display information that is independent of the patient, such as, for example, a coordinate system or an interactive dialogue box.

The patient monitor 122 may be configured to both mechanically and electrically couple with the docking station 110. The patient monitor 122 may receive power from the docking station 110, which itself can receive power from a power source (not shown) via a power line or cord. The power source may include, for example, the AC wiring of a hospital.

The docking station 110 may be mounted in a substantially fixed position. For example, the docking station 110 may be fixedly mounted to a wall within a hospital room in a single position by one or more plates, brackets, screws, bolts, or other mounting hardware and attachment devices. As another example, the docking 110 station may be configured to transition among multiple fixed positions. For example, in the illustrated embodiment, the docking station 110 is coupled to a mounting strip 822, which is in turn mounted to a wall (not shown) of a hospital room. The docking station 110 is capable of being adjusted upwardly or downwardly along a path constrained by one or more channels defined by the mounting strip 822 so as to transition among a variety of positions. In each such position, the docking station 110 can be fixed relative to the mounting strip 822. In some embodiments, the docking station 110 is coupled with the mounting strip 822 via a mounting plate or a mounting bracket (not shown), the position of which can be adjusted upwardly or downwardly within the channels in any suitable manner.

In other embodiments, the docking station 110 may be secured to a hospital bed (not shown), a mechanical arm (not shown), or any other suitable object. In some embodiments, a bottom surface of the docking station 110 is positioned at a height of from about five feet to about six feet above a floor of a hospital room so as to allow the patient monitor 122 to be viewed easily and/or to avoid interference with other objects in the room.

It will be understood by those having skill in the art that many changes may be made to the details of the above-described embodiments without departing from the underlying principles of the invention. The scope of the present invention should, therefore, be determined only by the following claims.

The invention claimed is:

1. A patient monitor system, comprising:
a plurality of docking stations, each docking station associated with a respective patient monitoring location;
a portable patient monitor configured to be selectively coupled with and selectively decoupled from the respective docking stations as a user transports the portable patient monitor among the patient monitoring locations, the portable patient monitor comprising:
a patient data acquisition unit for receiving patient data signals from one or more sensors attached to a patient; and
a processor for processing the patient data signals, the processor configured to:
detect a coupling of the portable patient monitor to a first docking station of the plurality of docking stations, the first docking station being associated with a first patient monitor location;
in response to a determination by the processor that the first patient monitor location is a non-transient hospital ward, prompt the user to select one or more first default configuration settings associated with the first patient monitor location;

in response to a user selection, load the selected one or more first default configuration settings into the patient monitor;

detect a coupling of the patient monitor to a second docking station of the plurality of docking stations, the second docking station being associated with a second patient monitor location;

in response to a determination by the processor that the second patient monitor location is a transient location where the patient is expected to remain for a relatively short period of time as compared to that spent in the first patient monitor location, maintain a current set of configuration settings in disregard to one or more second default settings, if any, associated with the second patient monitor location.

2. The system of claim 1, wherein the predetermined condition comprises a determination by the processor that a current set of configuration settings is different than the one or more first default configuration settings.

3. The system of claim 1, wherein the predetermined condition comprises a determination by the processor that the one or more first default configuration settings are optional settings.

4. The system of claim 1, wherein the predetermined condition comprises a determination by the processor that the portable patient monitor includes an unprotected setting that conflicts with the one or more first default settings.

5. The system of claim 1, wherein the first docking station comprises:
a power interface to provide power to the portable patient monitor while coupled thereto; and
a memory device for storing the one or more first default configuration settings corresponding to the first patient monitoring location.

6. The system of claim 5, wherein the processor is configured to load the selected one or more first default configuration settings into the portable patient monitor directly from the memory device in the first docking station.

7. The system of claim 1, wherein the first docking station comprises:
a power interface to provide power to the portable patient monitor while coupled thereto; and
a network interface to provide communication between the portable patient monitor and a network server.

8. The system of claim 7, wherein the processor is further configured to:
upon detection of the coupling of the portable patient monitor to the first docking station, determine a unique identification number associated with the first docking station;
communicate the unique identification number to the network server through the network interface; and
receive the one or more first default configuration settings from the network server through the network interface.

9. The system of claim 8, wherein the unique identification number is stored in a memory device within the first docking station.

10. The system of claim 8, wherein the unique identification number is a media access control (MAC) address associated with network interface.

11. The system of claim 8, wherein the portable patient monitor receives the unique identification number from the first docking station through a radio frequency identification (RFID) tag.

12. The system of claim 1, wherein the processor is configured to prompt the user by allowing the user to selectively choose any number of the one or more first default configuration settings for loading into the portable patient monitor.

13. The system of claim 1, wherein the portable patient monitor further comprises a user control for associating a current set of configuration settings with a coupled docking station.

14. The system of claim 13, wherein a user selection of the user control stores the current set of configuration settings into a memory device within the coupled docking station.

15. The system of claim 13, wherein a user selection of the user control stores the current set of configuration settings in a network server and associates the coupled docking station with the stored settings.

16. The system of claim 13, wherein at least one setting in the current set of configuration settings is protected such that a sufficient authorization level is required to change or ignore the protected setting.

17. A method for use by a patient monitor system including a portable patient monitor and a plurality of docking stations, the method comprising:
associating each of the plurality of docking stations with a respective patient monitoring location;
receiving patient data signals into the portable patient monitor from one or more sensors attached to a patient;
processing the patient data signals for display on the portable patient monitor;
detecting a coupling of the portable patient monitor to a first docking station of the plurality of docking stations, the first docking station being associated with a first patient monitor location;
in response to a to a determination by a processor that the first patient monitor location is a non-transient hospital ward, prompting the user to select one or more first default configuration settings associated with the first patient monitor location;
in response to a user selection, loading the selected one or more first default configuration settings into the portable patient monitor;
detecting a coupling of the portable patient monitor to a second docking station of the plurality of docking stations, the second docking station being associated with a second patient monitor location;
in response to a determination by the processor that the second patient monitor location is a transient location where the patient is expected to remain for a relatively short period of time as compared to that spent in the first patient monitor location, maintain a current set of configuration settings in disregard to one or more second default settings, if any, associated with the second patient monitor location.

* * * * *